United States Patent [19]

Schloemer et al.

[11] Patent Number: 5,651,367

[45] Date of Patent: Jul. 29, 1997

[54] PARAMETER DISTURBANCE RESPONSE APPARATUS

[75] Inventors: David E. Schloemer, Shawnee; Jack B. Sippel, II, Overland Park, both of Kans.; Ronald A. Spero, Kansas City, Mo.; Harold K. Hoffman, Jr., Overland Park, Kans.

[73] Assignee: Nellcor Incorporated, Pleasanton, Calif.

[21] Appl. No.: 504,399

[22] Filed: Jul. 19, 1995

[51] Int. Cl.⁶ .................................................. A61B 5/02
[52] U.S. Cl. ........................... 128/670; 128/672; 128/633; 128/696
[58] Field of Search ........................... 128/630, 637–639, 128/668, 670–675, 687, 725

[56] References Cited

U.S. PATENT DOCUMENTS 4,404,974  9/1983  Titus ............................. 128/670
5,309,908  5/1994  Friedman et al. ............. 128/633

*Primary Examiner*—Lee S. Cohen
*Assistant Examiner*—Stephen Huang
*Attorney, Agent, or Firm*—Nawrocki, Rooney & Sivertson

[57] ABSTRACT

This invention provides apparatus for collecting parameter disturbance information from each connected apparatus which can disturb measuring vital signs, and broadcasting a message regarding the disturbance and a coordinating clock signal to all apparatus. Connected sensors susceptible to parameter disturbances identify them from the message and suppress their audible alarm during an interval given in the message. This eliminates false audible alarms caused by such disturbances. The disturbance interval can be extended for later disturbances unless it is a new source or disturbance type and the alarm is already suppressed. A brickwall timer limits the total maximum suppressed interval to a safe maximum. A recovery timer allows a sensor to recover from a parameter disturbance before responding to a subsequent one.

6 Claims, 5 Drawing Sheets

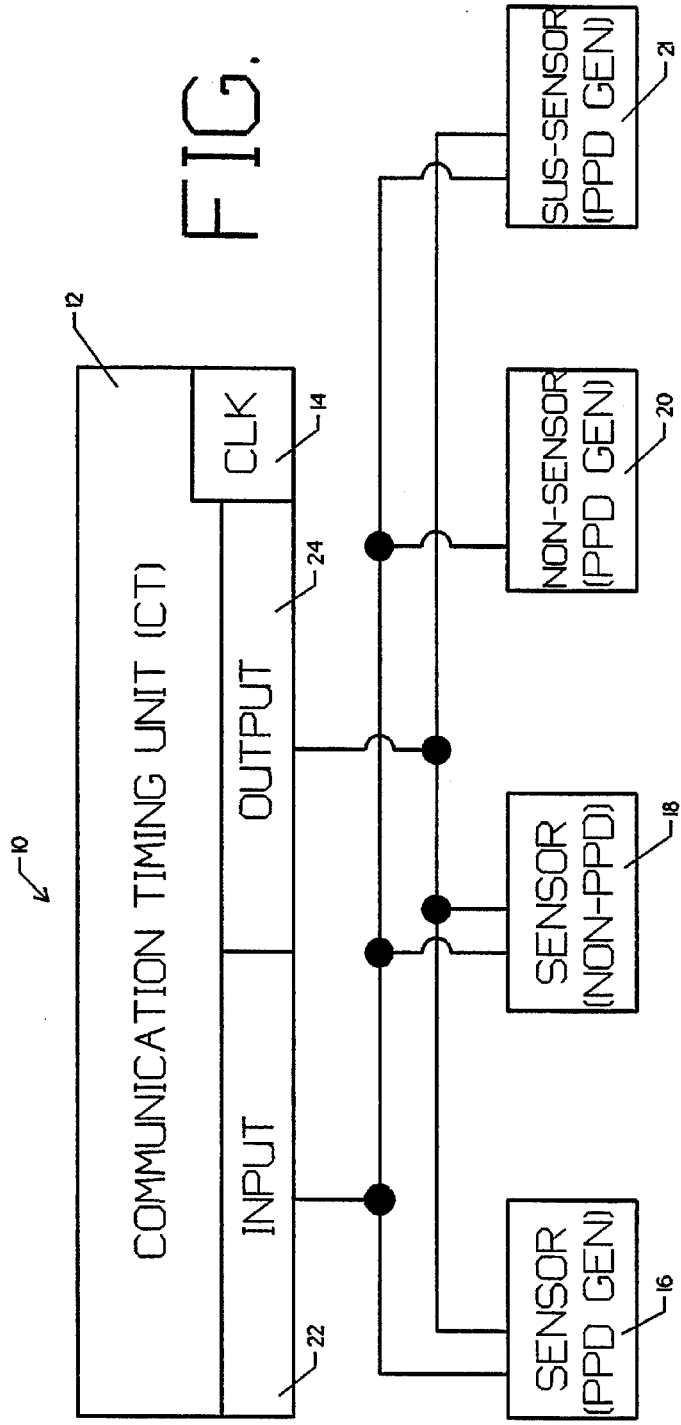

PARAMETER DISTURBANCE RESPONSE APPARATUS

FIELD OF THE INVENTION

The present invention relates to suppression of false audible alarms in any number of patient vital sign sensing apparatus interconnected with any number of devices which cause a disturbance and resulting false alarm.

DESCRIPTION OF RELATED ART

The problem of a patient monitoring system which includes a pulse oximeter sensor and a blood pressure module which inflates a cuff during its active cycle resulting in a false audible alarm by the pulse oximeter was addressed in Friedman et al. U.S. Pat. No. 5,309,908. Friedman et al., which is typical of the prior art, provides fixed interconnected logic elements which suppress the audible alarm of the pulse oximeter sensor and only during the time that the cuff inflation affects the pulse readings.

As with the prior art, this apparatus is severely limited in scope. In the actual clinical environment, a number of devices can cause disturbances in reading a given body vital sign during their operation. Similarly, a number of sensors may each be susceptible to various disturbances resulting in false indications. An example of equipment which can cause such disturbances and resulting errors in vital sign sensors includes electrocauterization and transcutaneous electrical nerve stimulation (TENS) apparatus. These produce intense electrical fields which can cause read-out errors in susceptible sensors.

Further, Friedman et al. does not address problems which may be presented in the future by additional apparatus which can produce disturbances resulting in reading errors in new vital sign sensing apparatus.

SUMMARY OF THE INVENTION

The instant invention addresses the problems of interconnection and interaction between any number of sensors and any number of devices which can produce an erroneous indication resulting in a false audible alarm in any one or more of these sensors. Further, the instant invention is open ended to permit adding new apparatus in the future, while still providing the protocol to eliminate false alarms caused by interaction between any of the previous or new devices.

Operation of certain equipment used in patient procedures create disturbances which can cause an error in the sensing of a vital sign by a sensor susceptible to the disturbance. Such a disturbance is hereafter herein referred to as a Patient Parameter Disturbance (PPD). A typical PPD results when a blood pressure monitor inflates a cuff for detecting blood pressure. A cuff inflation will cause a pulse or oxygen saturation detection sensor attached to the same limb to indicate a false pulse missing error. Other PPD generators include such devices as electrocauterization and TENS excitation apparatus. These produce intense electrical fields which can cause read-out errors in susceptible sensors.

A key feature of the present invention involves providing a common communication protocol for notifying each of the sensors concerning the occurrence, the timing, and the nature of each PPD event. In the preferred mode of practicing the present invention, a generalized PPD message format is defined, which can specify both timing and nature of any anticipated PDD event. A suitable PPD message is generated and transmitted to each sensor to provide notification of an approaching PPD event. If the proper PPD message is transmitted to each potentially effected sensor, the degree of centralization or decentralization of the communication functions may vary from one embodiment to another.

In a first, highly centralized approach, the instant invention may use a communication timing (CT) unit to interconnect all equipment which includes such devices as: sensors which are susceptible to a PPD, sensors which are not susceptible to a PPD but which create a PPD themselves, and non-sensing apparatus which create PPDs. The CT unit may provide a master timing signal for synchronous communication or the individual devices may communicate asynchronously using separate clocks. In the preferred mode, asynchronous communication operates effectively assuming a delivery delay of less than one second.

For this centralized approach, the Communicator Timer (CT) unit incorporates a communication network arranged to collect a PPD message from all PPD generating equipment, and broadcast this message to all connected apparatus. If synchronous communication is preferred, a time signal generated in the CT unit is also broadcast to all connected equipment to coordinate all PPD timing and any other data collected by any attached equipment.

Each connected device, which can produce a PPD, generates a PPD message describing the PPD characteristics, an estimate of the PPD duration, and a PPD identifier. Each PPD generating device also creates another message which identifies the PPD and signifies the termination of the event. These PPD messages are obtained, encoded and transmitted from each PPD generating apparatus over the CT network to the CT unit.

All of the PPD messages (plus a CT generated master time base, if synchronous transmission mode is used) are broadcast back over the same CT network to all connected equipment. These PPD messages provide information from all PPD generators to all susceptible sensors of all pertinent data regarding any PPD.

All sensors susceptible to a PPD, upon receiving a PPD message use the PPD identifier to identify the PPDs to which they are susceptible, and if susceptible, take appropriate action through the estimated duration of the PPD event.

The audible alarm signal of a susceptible sensor may be suppressed during a parameter disturbance interval, however, the visual alarm need not be suppressed to permit continual visual monitoring of all out-of-range conditions. The alarm suppression interval can be extended by later messages from the same apparatus or a new PPD message from a different apparatus which resets the parameter disturbance interval to the longest time interval. Because successive PPD messages could extend a PPD interval indefinitely, the maximum suppression time is preferably limited by a Brick Wall Timer (BWT). The BWT limits the maximum alarm suppression interval time to a predetermined length. This maximum alarm suppression time length, regardless of the number of successive PPD messages, though dependent upon the technology used and physiology involved, is preferably limited to 120 seconds, less a recovery timer interval of six seconds which will be described later, for adult or pediatric patient monitoring, and to 60 seconds, less six seconds for the Recovery Timer (RT) interval, for neonate monitoring. This ensures that audible alarms are not suppressed beyond a safe time interval.

The PPD interval ends either at the end of the PPD time interval after the indication, or earlier, if a stop message for that particular PPD generating apparatus is received at any time during the PPD interval. In either event, when the time of a PPD termination is determined, a Recovery Timer is started, which extends the alarm suppression interval six seconds beyond the PPD termination time. This avoids sounding an alarm before a disturbed parameter can return to normal.

The RT is also started by the BWT counting through its limit of 54 or 114 seconds to end the alarm suppression six seconds after the BW timer counts through zero. The BWT timer has 6 seconds subtracted from its total count to account for the amount of RT time.

In addition the above the PPD message is ignored if the sensor is out-of-range at the time of the receipt of any PPD start message when no alarm suppression has yet occurred.

The CT unit, used to collect the PPD messages from all PPD producers and broadcast the PPD messages and time to all attached devices, interconnects any number of PPD generators and sensors susceptible to PPD disturbances into a single system. This permits informing all susceptible sensing apparatus of any potential parameter disturbances and provides a time reference for all units. Sensors, whether or not they are affected by PPDs, and non-sensor apparatus, whether or not they create a PPD, can be added initially or later to the CT unit merely by incorporating the capabilities required to communicate with the unit. This open ended capability permits expanding the system to incorporate present or future apparatus, whatever its function, whenever the interchange of PPD or time information is deemed useful.

A second, highly decentralized approach distributes the functions of the CT unit amongst the PPD generators and suspectable sensors. In a preferred mode, all such devices are coupled via a token ring using a standard protocol such as ANSI 878.1. Each PPD generator broadcasts a PPD message as appropriate during its assigned time slot. Each susceptible sensor device reviews the PDD messages transmitted for those PDD events to which it is susceptible. According to this approach, each device is synchronously timed. In the most general case, a given PPD generator may also be a susceptible sensor device.

DESCRIPTION OF THE DRAWINGS

FIG. 1 is a block diagram of the apparatus including interconnected parameter disturbance generators and sensors using a centralized approach.

FIG. 2 is the arrangement of a parameter disturbance message word.

DETAILED DESCRIPTION OF THE PREFERRED EMBODIMENTS

Figure 3A:
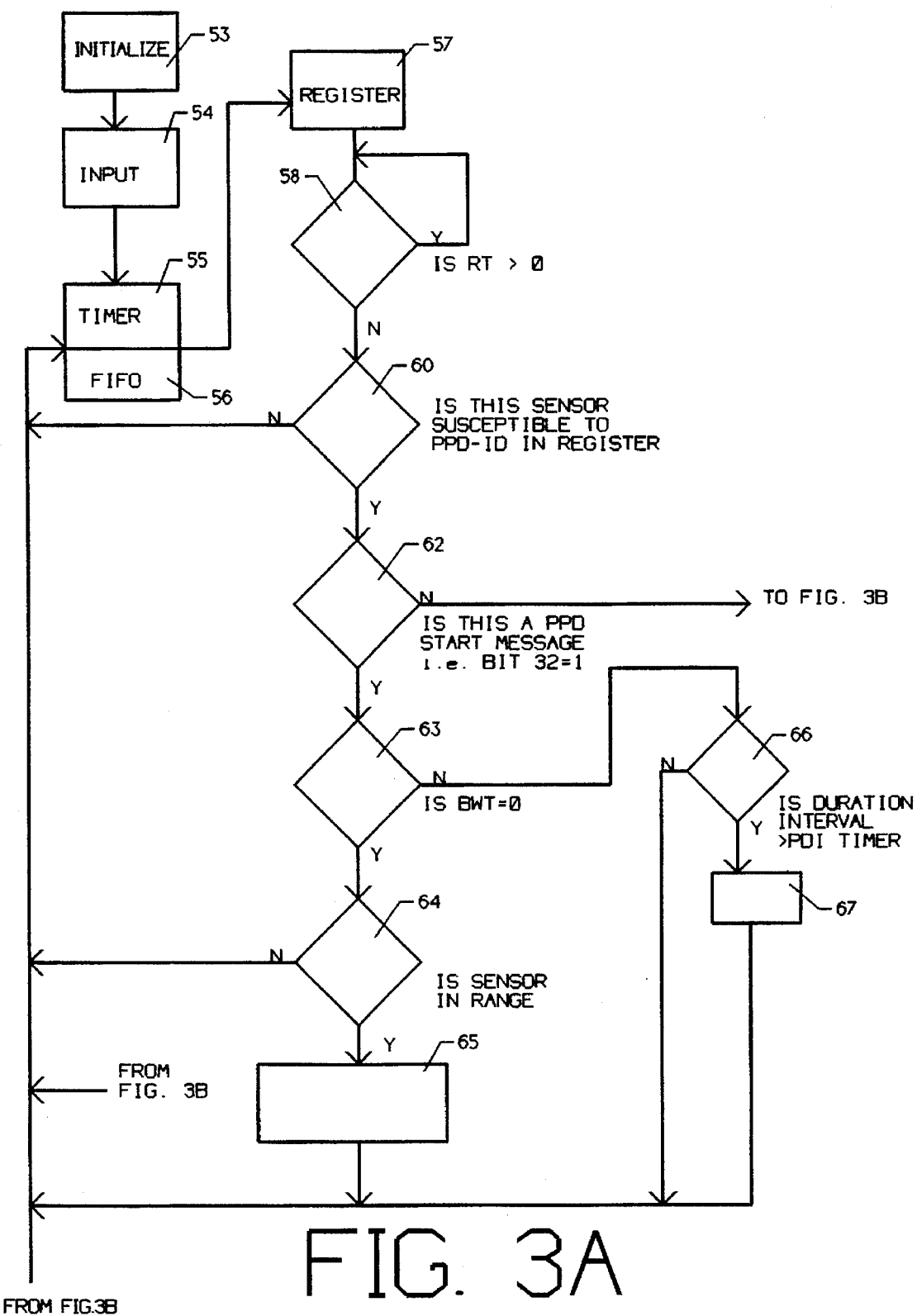
FIGS. 3A, 3B and 3C are block diagrams showing the logical processes and timing for operating the apparatus in the centralized mode.

A block diagram of the Parameter Disturbance Response 10 apparatus is shown in FIG. 1. Communication Timing unit (CT) 12 incorporates a clock 14 which generates a Master Time (MT) base. Sensor 16 will generate a patient parameter disturbance (PPD) in sensing a patient parameter but is not susceptible to any PPDs. Sensor 18 senses a patient parameter and is susceptible to PPDs but does not generate a PPD. Non-sensor apparatus 20 does not sense a patient parameter, and is therefore not susceptible to a PPD, but generates a PPD. Sensor 21 both generates and is susceptible to PPD events. This equipment is representative of the types of equipment which are connected to a CT unit 12. The CT unit 12 also includes input 22 and output 24. A Master time (MT) base derived from clock 14 is included in output 24. This MT base is used by all PPD susceptible equipment to coordinate timing information contained in the PPD message.

FIG. 2 shows the organization of the PPD message generated from either sensor 16, or any other PPD generator, or non-sensor 20 or 21 through input 22 and broadcast by output 24 of CT unit 12. The PPD message has an upper byte 26 and a lower byte 30 with a MSB 32. The upper byte 26 gives the parameter disturbance interval in seconds. The beginning of a PPD is indicated by a MSB of one in the lower byte 30, and the end of a PPD is indicated by a MSB of zero in the lower byte 30. The remaining bits of lower byte 30 gives the identifier of the disturbed parameter.

Figure 3B:
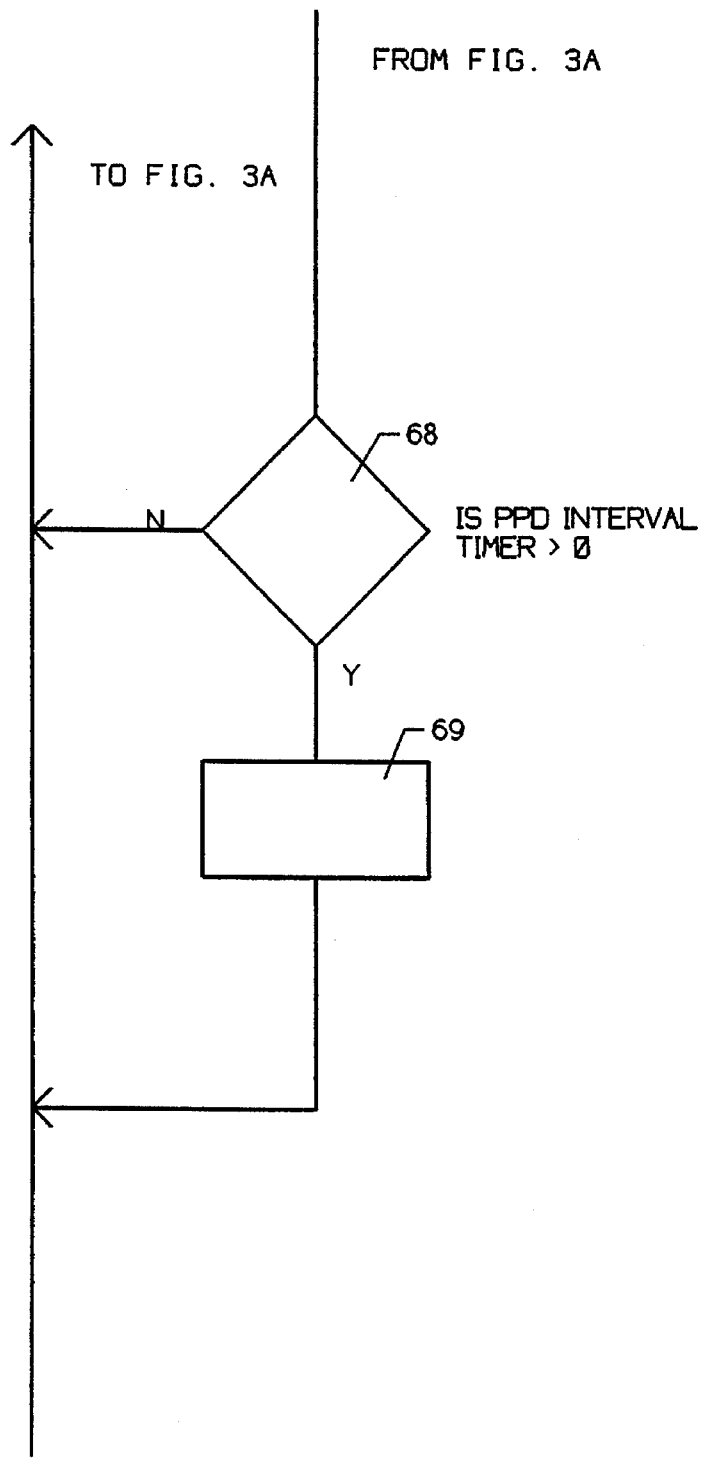
Figure 3C:
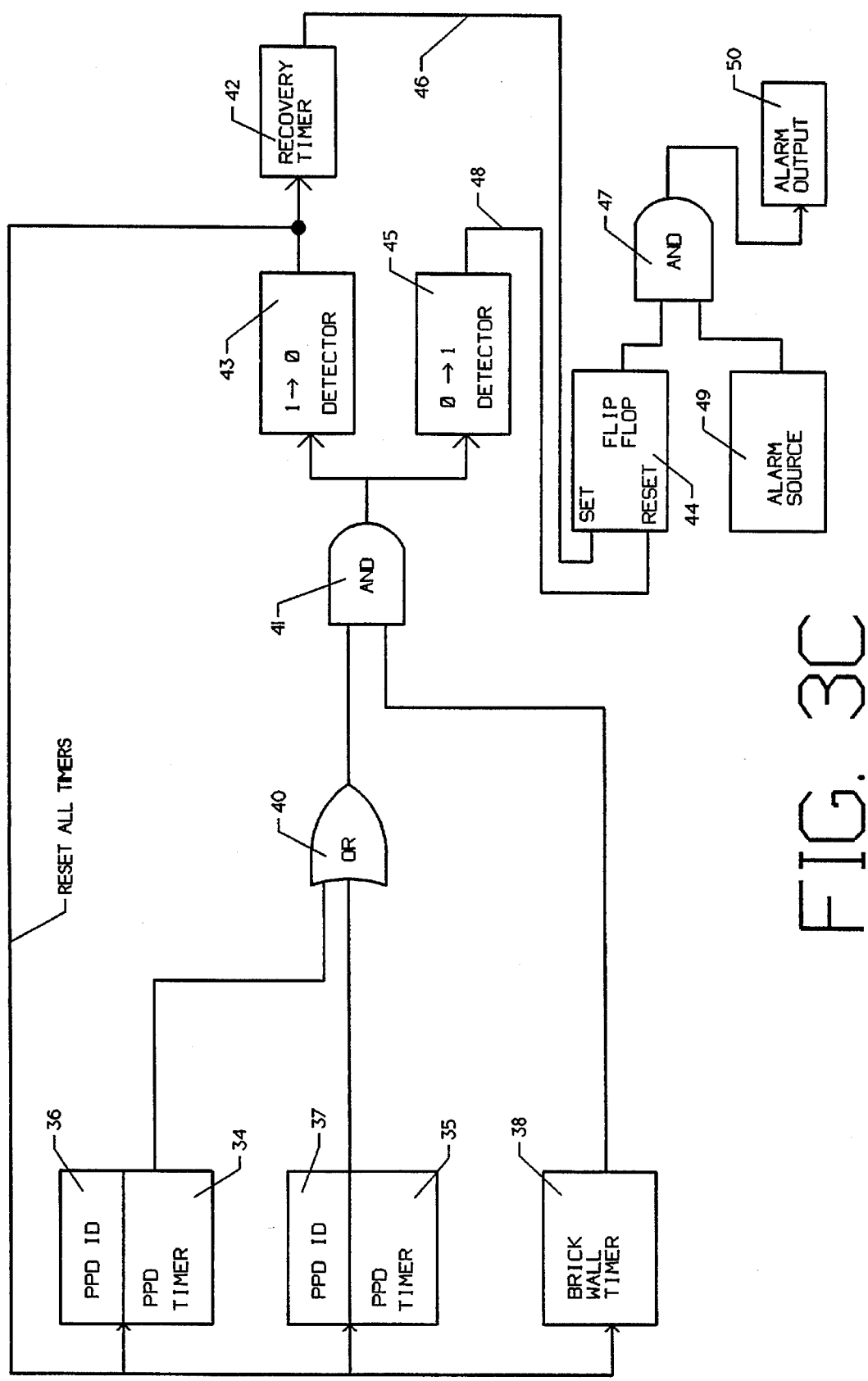

FIGS. 3A, 3B and 3C, which show logic flow charts and related timing, give the response of sensor 18, or any other susceptible sensor, to a PPD. In FIG. 3C, PPD interval timer 34 stores and then decrements the PPD estimated time interval in PPD message 25 in regular intervals through zero, and its register 36 stores the associated PPD identifier. PPD ID register 37 and PPD interval timer 35 provide for a second simultaneous PPD message. The outputs are or-ed and inverted by OR 40. Note that additional simultaneous PPD messages may be accommodated in this fashion. Brick Wall Timer (BWT) 38 and Recovery Timer (RT) 42 also decrement time in regular intervals from their respective initial values through zero. Upon reaching zero, RT 42 sets flip-flop 44 via line 46 enabling an alarm signal from alarm source 49 via AND 47 to generate an alarm via alarm output 50. The alarm is disabled by the clearing of flip-flop 44 via line 48 from transition detector 45. The transition of the output of AND 41 from 0 to 1 signifies that a PPD event has been signaled by a PPD start message. This transition occurs upon the output of BWT 38 and OR 40 both becoming 1. Similarly, transition detector 43 starts RT 42 upon a transition from 1 to 0 signifying the end of the PPD event or time-out via BWT 38.

Referring to FIGS. 3A and 3B and operating simultaneously with the circuitry of FIG. 3C, sensor 18 is initialized by block 53 and has an input 54 which receives PPD messages 25 from output 24 of CT unit 12 and stores them in FIFO 56. Block 53 sets BWT=0, PPDT=0, and RT=0. Messages 25 are entered into the top of FIFO 56 and are read from the bottom of the FIFO on a First In/First Out basis into a two byte storage register 57. FIFO 56 retains messages 25 until read, but while retained in the FIFO the PPD interval in all stored PPD messages are decremented by timer 55 at regular intervals. This ensures that if a PPD message is not read immediately, the PPD interval will not be effectively and inadvertently increased by the amount of time it remained in FIFO 56. Messages 25 are cleared from FIFO 56 as they are read into register 57. Register 57 does not need a timing capability because it is read and responded to in micro-seconds by a microprocessor used to generate the operations shown in FIGS. 3A, 3B and 3C.

When any of the following described tests require information about message 25, that information is obtained from register 57. Other data are obtained as implied from pre-stored data in other registers or from timer registers. As an example, test 60 requires information regarding to which PPD disturbances a particular sensor is susceptible. These identifiers are prestored in as many registers as required and all compared successively with the PPD identifier from the PPD message in this test. While the tests and various other operations, as shown in FIGS. 3A and 3B, are being performed in the sequence shown, the various timers and logic of FIG. 3C are operating independently.

The system is arranged such that until a PPD message 25 is received the system waits for a word to be entered into FIFO 56. When a message 25 is entered into FIFO 56 that message is then read from the FIFO into register 57.

Test 58 determines whether RT is greater than zero. If yes, control is maintained. If not, control is given to test 60 which uses the PPD identification information of message 25 loaded into register 57 to determine whether the sensor reading the message is susceptible to a disturbance from the identified disturbance source. The question of Test 60 is: Is this sensor susceptible to the identified PPD? If the answer is no, the next word in FIFO 56 is read. If FIFO 56 is empty the process is again halted until another message 25 is received, at which time the next PPD message in the FIFO is stored in register 57 and the above described sequence repeated.

Test 62 asks the question: Is the MSB of the lower byte one? A no indicates a PPD stop message and control is transferred to test 68. If the answer is yes, the PPD message is a start message and control is given to test 63 which determines whether BWT is zero.

When test 63 results in a yes, test 64 determines whether the sensor is within range before the PPD disturbance is entered into the system. Test 64 asks the question: Is this sensor in range? If the answer is no, control is returned to process the next PPD message. If the answer is yes, process 65 sets the PPD ID 36 or 37 from register 57, starts BWT at the maximum suppression time, and transfers the PPD event duration from register 57 to timer 34 or 35. If the answer to test 62 is yes (i.e. stop message), test 68 is performed. The question of Test 68 is: Is the PPD interval timer greater than zero? If the answer is yes, this is a normal termination and control is given to process 69 before returning to accommodate the next PPD message. Process 69 starts RT, sets BWT 38 to zero, and sets the PPD timer 34 or 35 to zero. If the answer is no, the next available word in FIFO 56 is read.

Test 66 asks the question: Is the PPD interval in register 57 greater than the current PPD interval timer 34 or 35 value? If the answer is no the interval stated is smaller than that currently in the PPD interval timer 34 and the next available word in FIFO 56 is read. If the answer is yes, then block 67 is executed where PPD interval timer 34 or 35 is set to the PPD interval stored in register 57 to extend the PPD interval, the PPD identifier stored in register 57 is read into PPD identification register 36 or 37 of PPD interval timer 34 or 35, and the next available word in FIFO 56 is read.

As shown in FIG. 3C, if during the above operations either all PPD interval timers (34 and 35), or BWT timer 38 decrement through zero from their initial value then Recovery Timer (RT) timer 42 will be started. When RT timer 42 decrements through zero from its initial value then Flip/Flop 44 is set which will enable Alarm 50 and permit it to sound.

This sequence of operations, while expressed as a series of test questions plus timing sequences, covers the necessary operations for this equipment. Any appropriate microprocessor can be coded with instructions to accomplish the operations described above by one skilled in the computer art.

This apparatus and procedure for operating the same describes a complete structure and apparatus for sensors, whose accuracy is susceptible to certain PPD disturbances, to mute their alarms during those particular PPD disturbances in order to avoid false alarms. Additional important features include means to extend the disturbance interval limit for repeat or new disturbances, means to limit the total disturbance interval to avoid muting the alarm beyond a safe interval, and recovery timer means which extends the disturbance interval to allow the sensor to recover from a disturbance to improve its performance. These features are important for certain patient procedures using a variety of devices. A number of the additional features described above can be eliminated under certain conditions, for example, when there is only one PPD generator or type of PPD generator PPD identification can be eliminated, or if successive and different PPDs can not occur within a given PPD disturbance interval then the extension of the PPD disturbance interval is unnecessary.

Figure 4:
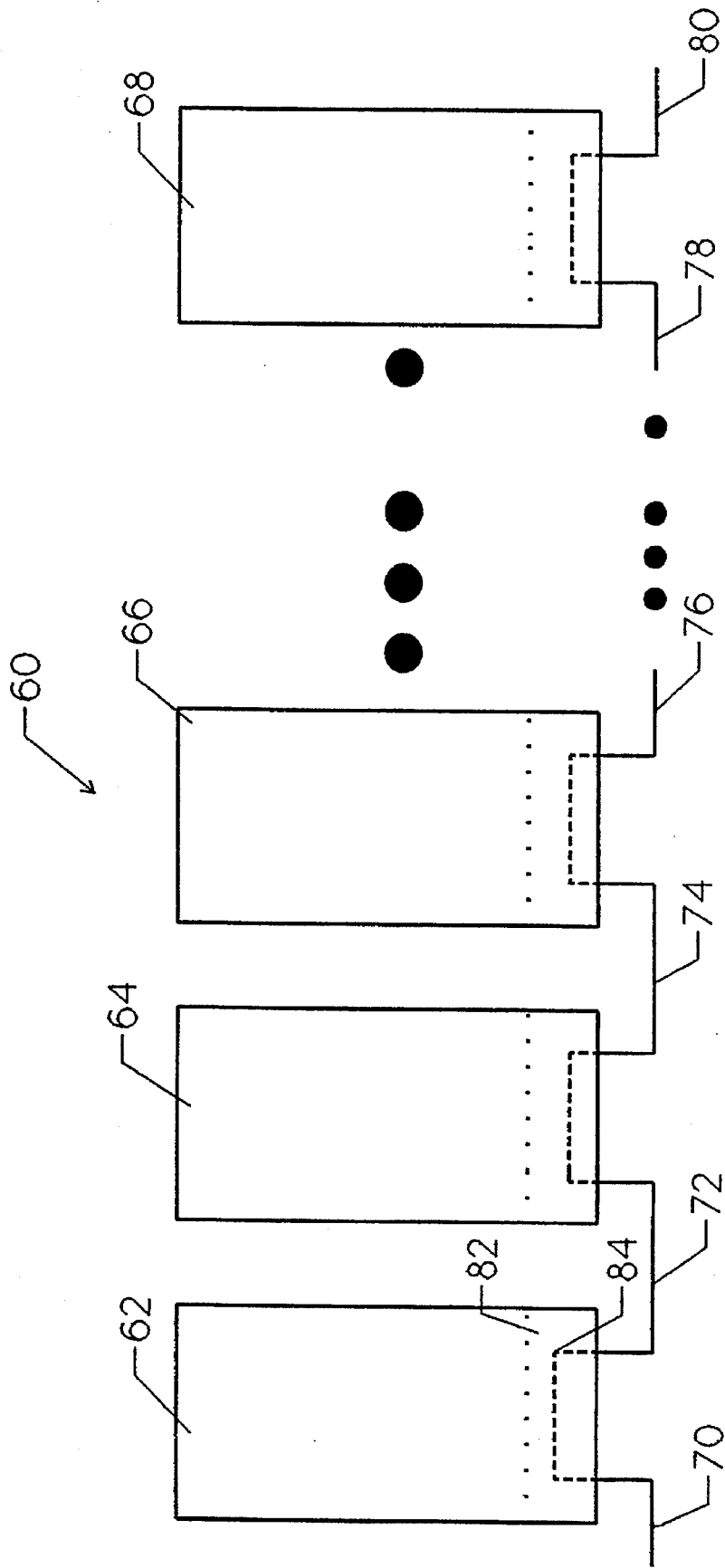
FIG. 4 shows an alternative embodiment utilizing the decentralized approach and asynchronous timing.

As described above, the functions of the Communications Timing (CT) unit may be highly centralized as in the embodiment of FIG. 1. FIG. 4 shows a system 60 wherein these functions are highly decentralized. System 60 contains a number of devices consisting of susceptible sensors and PPD generators as in the above centralized example. For clarity, only devices 62, 64, 66, and 68 are shown.

System 60 has each of the devices (i.e. devices 62, 64, 66, and 68) coupled in a token ring employing a standard interface protocol (e.g. ANSI 878.1). This is most easily implemented using a "daisy-chain" approach as shown. As it is added to system 60, device 62 is coupled into the daisy-chain via cable 70 to an existing device (not shown). Similarly, device 64 is coupled via cable 72, device 66 is coupled via cable 74, and device 68 is coupled via 76 through devices not shown and through cable 80.

Interface circuitry 82 of device 62 provides the electrical and functional interface between device 62 and the ANSI standard token ring. This circuitry is readily known in the art and enables device 62 to transmit PPD messages if it is a PPD generator and to receive and decode PPD messages if device 62 is a susceptible sensor. The other devices of system 60 are similarly equipped with appropriate interface circuitry.

While this invention has been described with respect to specific embodiments, this description is not intended to be construed in a limiting sense. Various modifications of the illustrative embodiments, as well as other embodiments of the invention, will be apparent to persons skilled in the art upon reference to this description within the scope of the appended claims.

We claim:

1. In a patient monitoring system having a plurality of devices wherein at least one of said devices is a patient parameter disturbance generator which generates a patient parameter disturbance event and at least one of said devices is a susceptible sensor which can cause an error condition as a result of said patient parameter disturbance event, an improvement to the system comprising:

notifying means coupled to said plurality of devices for notifying said at least one susceptible sensor of the generation of said patient parameter disturbance event; wherein said notifying means is decentralized.

2. In a patient monitoring system having a plurality of devices wherein at least one of said devices is a patient parameter disturbance generator which generates a patient parameter disturbance event and at least one of said devices is a susceptible sensor which can cause an error condition as a result of said patient parameter disturbance event, an improvement to the system comprising:

notifying means coupled to said plurality of devices for notifying said at least one susceptible sensor of the generation of said patient parameter disturbance event; wherein said notifying means is adapted to couple to an additional patient parameter disturbance generator; wherein said notifying means is decentralized.

3. In a patient monitoring system having a plurality of devices wherein at least one of said devices is a patient parameter disturbance generator which generates a patient parameter disturbance event and at least one of said devices is a susceptible sensor which can cause an error condition as a result of said patient parameter disturbance event, an improvement to the system comprising:

notifying means coupled to said plurality of devices for notifying said at least one susceptible sensor of the generation of said patient parameter disturbance event; wherein said notifying means is adapted to couple to an additional susceptible sensor; wherein said notifying means is decentralized.

4. In a patient monitoring system having a plurality of devices wherein at least one of said devices is a patient parameter disturbance generator which generates a patient parameter disturbance event and at least one of said devices is a susceptible sensor which can cause an error condition as a result of said patient parameter disturbance event, an improvement to the system comprising:

notifying means coupled to said plurality of devices for notifying said at least one susceptible sensor of the generation of said patient parameter disturbance event; wherein said notifying means is adapted to couple to an additional patient parameter disturbance generator; wherein said notifying means is adapted to couple to an additional susceptible sensor, and wherein said notifying means is decentralized.

5. A patient monitoring system comprising:

a. a patient parameter generator which causes a patient parameter disturbance event;

b. a susceptible sensor which is susceptible of producing an error as a result of a patient parameter disturbance event; and c. notifying means coupled to said patient parameter disturbance generator and said susceptible sensor for notifying said susceptible sensor of said patient parameter disturbance event, wherein said notifying means is adapted to couple to an additional patient parameter disturbance generator; wherein said notifying means is decentralized.

6. A patient monitoring system comprising:

a. a patient parameter disturbance generator which causes a patient parameter disturbance event;

b. a susceptible sensor which is susceptible of producing an error as a result of a patient parameter disturbance event; and c. notifying means coupled to said patient parameter disturbance generator and said susceptible sensor for notifying said susceptible sensor of said patient parameter disturbance event, wherein said notifying means is adapted to couple to an additional susceptible sensor; and wherein said notifying means is decentralized.

* * * * *